United States Patent
Grusin et al.

(10) Patent No.: US 10,575,883 B2
(45) Date of Patent: Mar. 3, 2020

(54) ACTIVE FRACTURE COMPRESSION IMPLANTS

(71) Applicant: Smith & Nephew, Inc., Memphis, TN (US)

(72) Inventors: Nathaniel K. Grusin, Germantown, TN (US); Kohsuke Watanabe, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 240 days.

(21) Appl. No.: 15/747,257

(22) PCT Filed: Dec. 14, 2015

(86) PCT No.: PCT/US2015/065450
§ 371 (c)(1),
(2) Date: Jan. 24, 2018

(87) PCT Pub. No.: WO2016/100158
PCT Pub. Date: Jun. 23, 2016

(65) Prior Publication Data
US 2018/0221066 A1      Aug. 9, 2018

Related U.S. Application Data

(60) Provisional application No. 62/092,006, filed on Dec. 15, 2014.

(51) Int. Cl.
*A61B 17/74* (2006.01)
*A61B 17/86* (2006.01)
*A61B 17/88* (2006.01)

(52) U.S. Cl.
CPC .......... *A61B 17/746* (2013.01); *A61B 17/744* (2013.01); *A61B 17/8685* (2013.01);
(Continued)

(58) Field of Classification Search
CPC .............. A61B 17/746; A61B 17/7085; A61B 17/7082; A61B 17/7091; A61B 17/8875;
(Continued)

(56) References Cited

U.S. PATENT DOCUMENTS

| | | | |
|---|---|---|---|
| 1,025,008 A | 4/1912 | Miner | |
| 2,077,804 A | 4/1937 | Monroe | |

(Continued)

FOREIGN PATENT DOCUMENTS

| | | |
|---|---|---|
| CN | 103815957 A | 5/2014 |
| EP | 0760231 A1 | 3/1997 |

(Continued)

OTHER PUBLICATIONS

European Search Report for EP Patent Application No. 15823052.4, dated May 3, 2019.

(Continued)

*Primary Examiner* — Lynnsy M Summit
*Assistant Examiner* — Tara Rose E Carter

(57) ABSTRACT

An assembly and method are disclosed. The assembly includes an orthopaedic implant and an active compression member. The implant has a compression screw hole with a step and the active compression member includes an outer tube and an inner slide. The tube and slide allow the proximal end portion and the distal end portion to move relative to one another. The method includes inserting a guide wire, placing a drill over the guide wire and drilling into a femur, tapping the drilled hole, using a compression device to reduce the fracture using the orthopaedic implant step, and inserting one or more active compression members into the tapped hole.

1 Claim, 8 Drawing Sheets

(52) U.S. Cl.
CPC ...... *A61B 17/8869* (2013.01); *A61B 17/8872* (2013.01); *A61B 17/8625* (2013.01)

(58) Field of Classification Search
CPC ............ A61B 17/7076; A61B 17/7086; A61B 17/7083; A61B 17/8872
See application file for complete search history.

(56) References Cited

U.S. PATENT DOCUMENTS

| | | |
|---|---|---|
| 2,381,050 A | 8/1945 | Hardinge |
| 2,397,545 A | 4/1946 | Hardinge |
| 2,414,882 A | 1/1947 | Longfellow |
| 2,490,364 A | 12/1949 | Livingston |
| 2,511,051 A | 6/1950 | Dzus |
| 3,051,169 A | 8/1962 | Leonard et al. |
| 3,433,220 A | 3/1969 | Zickel |
| 3,489,143 A | 1/1970 | Halloran |
| 4,456,005 A | 6/1984 | Lichty |
| 4,617,922 A | 10/1986 | Griggs |
| 4,621,629 A | 11/1986 | Koeneman |
| 4,632,100 A | 12/1986 | Somers et al. |
| 4,640,271 A | 2/1987 | Lower |
| 4,708,132 A | 11/1987 | Silvestrini |
| 4,741,330 A | 5/1988 | Hayhurst |
| 4,773,406 A | 9/1988 | Spector et al. |
| 4,889,110 A | 12/1989 | Galline et al. |
| 4,904,467 A | 2/1990 | Schwulera |
| 4,905,680 A | 3/1990 | Tunc |
| 4,940,467 A | 7/1990 | Tronzo |
| 4,959,064 A | 9/1990 | Engelhardt |
| 5,019,079 A | 5/1991 | Ross |
| 5,041,116 A | 8/1991 | Wilson |
| 5,061,137 A | 10/1991 | Gourd |
| 5,100,405 A | 3/1992 | McLaren |
| 5,100,640 A | 3/1992 | Dittmer et al. |
| 5,102,276 A | 4/1992 | Gourd |
| 5,116,336 A | 5/1992 | Frigg |
| 5,116,340 A | 5/1992 | Songer et al. |
| 5,122,133 A | 6/1992 | Evans |
| 5,127,914 A | 7/1992 | Calderale et al. |
| 5,129,901 A | 7/1992 | Decoste |
| 5,141,520 A | 8/1992 | Goble et al. |
| 5,207,753 A | 5/1993 | Badrinath |
| 5,217,462 A | 6/1993 | Asnis et al. |
| 5,269,784 A | 12/1993 | Mast |
| 5,300,075 A | 4/1994 | Gordon |
| 5,306,290 A | 4/1994 | Martins et al. |
| 5,324,292 A | 6/1994 | Meyers |
| 5,336,028 A | 8/1994 | Yamamoto |
| 5,338,139 A | 8/1994 | Swanstrom |
| 5,364,398 A | 11/1994 | Chapman et al. |
| 5,368,605 A | 11/1994 | Miller, Jr. |
| 5,382,124 A | 1/1995 | Frattarola |
| 5,409,493 A | 4/1995 | Greenberg |
| 5,417,692 A | 5/1995 | Goble et al. |
| 5,423,820 A | 6/1995 | Miller et al. |
| 5,431,660 A | 7/1995 | Burke |
| 5,462,547 A | 10/1995 | Weigum |
| 5,507,801 A | 4/1996 | Gisin et al. |
| 5,520,691 A | 5/1996 | Branch |
| 5,591,207 A | 1/1997 | Coleman |
| 5,601,553 A | 2/1997 | Trebing et al. |
| 5,607,426 A | 3/1997 | Ralph et al. |
| 5,611,801 A | 3/1997 | Songer |
| 5,632,745 A | 5/1997 | Schwartz |
| 5,643,267 A | 7/1997 | Hitomi et al. |
| 5,702,397 A | 12/1997 | Goble et al. |
| 5,709,687 A | 1/1998 | Pennig |
| 5,725,582 A | 3/1998 | Bevan et al. |
| 5,809,849 A | 9/1998 | Coffey et al. |
| 5,827,285 A | 10/1998 | Bramlet |
| 5,893,850 A | 4/1999 | Cachia |
| 5,893,859 A | 4/1999 | Marin et al. |
| 5,928,236 A | 7/1999 | Augagneur et al. |
| 5,954,722 A | 9/1999 | Bono |
| 5,964,760 A | 10/1999 | Richelsoph |
| 5,964,763 A | 10/1999 | Incavo et al. |
| 5,976,139 A | 11/1999 | Bramlet |
| 5,984,925 A | 11/1999 | Apgar |
| 5,993,477 A | 11/1999 | Vaitekunas et al. |
| 5,997,538 A | 12/1999 | Asnis et al. |
| 5,997,541 A | 12/1999 | Schenk |
| 6,027,523 A | 2/2000 | Schmieding |
| 6,033,429 A | 3/2000 | Magovern |
| 6,039,740 A | 3/2000 | Olerud |
| 6,050,998 A | 4/2000 | Fletcher |
| 6,093,188 A | 7/2000 | Murray |
| 6,143,037 A | 11/2000 | Goldstein et al. |
| 6,171,310 B1 | 1/2001 | Giordano et al. |
| 6,174,006 B1 | 1/2001 | Burt |
| 6,183,474 B1 | 2/2001 | Bramlet et al. |
| 6,235,062 B1 | 5/2001 | Gramnas |
| 6,245,071 B1 | 6/2001 | Pierson |
| 6,251,111 B1 | 6/2001 | Barker et al. |
| 6,283,965 B1 | 9/2001 | Ballier et al. |
| 6,319,254 B1 | 11/2001 | Giet et al. |
| 6,348,053 B1 | 2/2002 | Cachia |
| 6,368,326 B1 | 4/2002 | Dakin et al. |
| 6,524,313 B1 | 2/2003 | Fassier et al. |
| 6,602,293 B1 | 8/2003 | Biermann et al. |
| 6,605,090 B1 | 8/2003 | Trieu et al. |
| 6,610,067 B2 | 8/2003 | Tallarida et al. |
| 6,629,534 B1 | 10/2003 | St. Goar et al. |
| 6,632,224 B2 | 10/2003 | Cachia et al. |
| 6,656,184 B1 | 12/2003 | White et al. |
| 6,656,185 B2 | 12/2003 | Gleason et al. |
| 6,679,883 B2 | 1/2004 | Hawkes et al. |
| 6,685,706 B2 | 2/2004 | Padget et al. |
| 6,695,844 B2 | 2/2004 | Bramlet et al. |
| 6,736,819 B2 | 5/2004 | Tipirneni |
| 6,840,953 B2 | 1/2005 | Martinek |
| 6,887,243 B2 | 5/2005 | Culbert |
| 6,887,271 B2 | 5/2005 | Justin et al. |
| 6,890,333 B2 | 5/2005 | von Hoffmann et al. |
| 6,902,567 B2 | 6/2005 | Del Medico |
| 6,908,465 B2 | 6/2005 | von Hoffmann et al. |
| 6,984,241 B2 | 1/2006 | Lubbers et al. |
| 7,008,428 B2 | 3/2006 | Cachia et al. |
| 7,033,363 B2 | 4/2006 | Powell |
| 7,070,601 B2 | 7/2006 | Culbert et al. |
| 7,090,686 B2 | 8/2006 | Nobles et al. |
| 7,094,239 B1 | 8/2006 | Michelson |
| 7,094,240 B2 | 8/2006 | Molz, IV et al. |
| 7,135,023 B2 | 11/2006 | Watkins et al. |
| 7,143,308 B2 | 11/2006 | Tseng et al. |
| 7,147,639 B2 | 12/2006 | Berki et al. |
| 7,163,542 B2 | 1/2007 | Ryan |
| 7,172,595 B1 | 2/2007 | Goble |
| 7,189,251 B2 | 3/2007 | Kay |
| 7,254,281 B2 | 8/2007 | Slavin |
| 7,353,547 B2 | 4/2008 | Diethelm et al. |
| 7,476,254 B2 | 1/2009 | White et al. |
| 7,503,919 B2 | 3/2009 | Shaw |
| 7,591,823 B2 | 9/2009 | Tipirneni |
| 7,591,840 B2 | 9/2009 | Suddaby |
| 7,618,418 B2 | 11/2009 | Malandain |
| 7,618,451 B2 | 11/2009 | Berez et al. |
| 7,637,949 B2 | 12/2009 | Hart |
| 7,641,677 B2 | 1/2010 | Weiner et al. |
| 7,678,138 B2 | 3/2010 | Fitts et al. |
| 7,771,428 B2 | 8/2010 | Siravo et al. |
| 7,824,429 B2 | 11/2010 | Culbert et al. |
| 7,901,412 B2 | 3/2011 | Tipirneni |
| 7,912,550 B2 | 3/2011 | Scheiner |
| 7,914,532 B2 | 3/2011 | Shaver et al. |
| 7,951,176 B2 | 5/2011 | Grady, Jr. et al. |
| 7,972,366 B2 | 7/2011 | Richelsoph et al. |
| 7,981,114 B2 | 7/2011 | Zander |
| 8,109,936 B2 | 2/2012 | Tipirneni |
| 8,353,941 B2 | 1/2013 | Fricker et al. |
| 8,679,167 B2 | 3/2014 | Tipirneni et al. |
| 8,702,768 B2 | 4/2014 | Tipirneni |
| 8,828,067 B2 | 9/2014 | Tipirneni et al. |
| 2002/0198527 A1 | 12/2002 | Muckter |

(56) References Cited

U.S. PATENT DOCUMENTS

| | | |
|---|---|---|
| 2003/0036761 A1 | 2/2003 | Smothers et al. |
| 2003/0083658 A1 | 5/2003 | Hawkes et al. |
| 2003/0187440 A1 | 10/2003 | Richelsoph et al. |
| 2003/0216780 A1 | 11/2003 | Fitts et al. |
| 2004/0097943 A1 | 5/2004 | Hart |
| 2004/0127906 A1 | 7/2004 | Culbert et al. |
| 2004/0236424 A1 | 11/2004 | Berez et al. |
| 2004/0243129 A1 | 12/2004 | Moumene et al. |
| 2005/0010226 A1 | 1/2005 | Grady, Jr. et al. |
| 2005/0234456 A1 | 10/2005 | Malandain |
| 2005/0263549 A1 | 12/2005 | Scheiner |
| 2006/0036254 A1* | 2/2006 | Lim .................. A61B 17/7086 606/86 R |
| 2006/0129148 A1 | 6/2006 | Simmons et al. |
| 2006/0147127 A1 | 7/2006 | Slavin |
| 2006/0161805 A1 | 7/2006 | Tseng et al. |
| 2006/0167457 A1 | 7/2006 | Suddaby |
| 2006/0190001 A1 | 8/2006 | Powell |
| 2006/0248638 A1 | 11/2006 | Diethelm et al. |
| 2007/0055249 A1 | 3/2007 | Jensen et al. |
| 2007/0123878 A1 | 5/2007 | Shaver et al. |
| 2007/0162019 A1 | 7/2007 | Burns et al. |
| 2007/0162026 A1 | 7/2007 | Tipirneni et al. |
| 2007/0190230 A1 | 8/2007 | Trieu et al. |
| 2007/0233100 A1 | 10/2007 | Metzinger |
| 2007/0260248 A1 | 11/2007 | Tipirneni |
| 2007/0270847 A1 | 11/2007 | Shaw |
| 2007/0276382 A1 | 11/2007 | Mikhail et al. |
| 2008/0086144 A1 | 4/2008 | Zander |
| 2008/0147126 A1 | 6/2008 | Tipirneni et al. |
| 2008/0147127 A1 | 6/2008 | Tipirneni et al. |
| 2008/0243132 A1 | 10/2008 | Tipirneni et al. |
| 2008/0243191 A1 | 10/2008 | Tipirneni et al. |
| 2008/0255555 A1 | 10/2008 | Justis et al. |
| 2008/0255621 A1 | 10/2008 | Fricker et al. |
| 2008/0300636 A1 | 12/2008 | Carli et al. |
| 2009/0048606 A1 | 2/2009 | Tipirneni et al. |
| 2009/0131936 A1 | 5/2009 | Tipirneni et al. |
| 2009/0131990 A1 | 5/2009 | Tipirneni et al. |
| 2009/0131991 A1 | 5/2009 | Tipirneni et al. |
| 2009/0177199 A1 | 7/2009 | Tipirneni |
| 2009/0198288 A1 | 8/2009 | Hoof et al. |
| 2009/0254089 A1 | 10/2009 | Tipirneni et al. |
| 2009/0254129 A1 | 10/2009 | Tipirneni et al. |
| 2009/0306718 A1 | 12/2009 | Tipirneni et al. |
| 2010/0036443 A1* | 2/2010 | Hutton ............... A61B 17/7032 606/86 R |
| 2010/0114097 A1 | 5/2010 | Siravo et al. |
| 2010/0268285 A1 | 10/2010 | Tipirneni et al. |
| 2010/0312245 A1 | 12/2010 | Tipirneni et al. |
| 2010/0312292 A1 | 12/2010 | Tipirneni et al. |
| 2011/0034925 A1 | 2/2011 | Tipirneni et al. |
| 2011/0295252 A1 | 12/2011 | Tipirneni et al. |
| 2014/0046388 A1* | 2/2014 | Reichen ............. A61B 17/7083 606/86 A |
| 2016/0106491 A1 | 4/2016 | Zhang et al. |

FOREIGN PATENT DOCUMENTS

| | | |
|---|---|---|
| EP | 2626019 A1 | 8/2013 |
| FR | 2784019 A3 | 4/2000 |
| WO | 2000067652 A2 | 11/2000 |
| WO | 2007125561 A1 | 11/2007 |
| WO | 2009015075 A2 | 1/2009 |
| WO | 12024465 A2 | 2/2012 |
| WO | 2014/145979 A1 | 9/2014 |

OTHER PUBLICATIONS

International Search Report and Written Opinion for International Application No. PCT/US2015/065450, dated May 31, 2016.
Office Action with English Translation for Chinese Patent Application No. 201580068560.3 dated Oct. 18, 2018; 20 pages.

* cited by examiner

ACTIVE FRACTURE COMPRESSION IMPLANTS

CROSS-REFERENCE TO RELATED APPLICATIONS

This application is a United States National Phase filing of International Application No. PCT/US2015/065450, filed Dec. 14, 2015 which claims the benefit of U.S. Provisional Application No. 62/092,006, filed Dec. 15, 2014. The disclosure of each application is incorporated by reference in its entirety.

BACKGROUND OF THE INVENTION

The present invention generally relates to a system for coupling bone portions across a fracture and, more specifically, to an intramedullary nail or plate and screw assembly used to treat fractures of long bones, such as the femur, humerus, and tibia, fractures of the intertrochanteric region, and various periarticular fractures of these and other bones.

There are a variety of devices used to treat fractures of the femur, humerus, tibia, and other long bones. For example, fractures of the femoral neck, head, and intertrochanteric region have been successfully treated with a variety of compression screw assemblies, which include generally a compression plate having a barrel member, a lag screw and a compressing screw. In such systems, the compression plate is secured to the exterior of the femur, and the barrel member is inserted in a predrilled hole in the direction of the femoral head. The lag screw has a threaded end, or another mechanism for engaging bone, and a smooth portion. The lag screw is inserted through the barrel member so that it extends across the break and into the femoral head. The threaded portion engages the femoral head. The compression screw connects the lag screw to the plate. By adjusting the tension of the compression screw, the compression (reduction) of the fracture can be varied. The smooth portion of the lag screw is free to slide through the barrel member to permit the adjustment of the compression screw. Some assemblies of the prior art use multiple screws to prevent rotation of the lag screw relative to the compression plate and barrel member and also to prevent rotation of the femoral head on the lag screw.

Compression plates may be of the locking or non-locking variety. Generally, non-locking bone plates have a plurality of non-threaded holes for receiving non-locking screws. Non-locking screws are screws that are not secured to a plate. Non-locking plates depend on friction between the screw and bone for stability. Therefore, non-locking plates have a low resistance to shear force which can cause screw loosening, but non-locking plates have the advantage of allowing the screw to compress the bone across a fracture site.

In contrast, a locking plate has threads on an inner surface of the screw holes that correspond to threads on an outer surface of a head of the locking screw. Locking plates and screws have a fixed relationship that the stability at the screw and plate hole does not rely on screw purchase in bone. As such, locking screws have a high resistance to shear force, which can reduce bone vascular damage and result in better clinical results, but locking plates have a disadvantage in that the screw head engages the threaded hole on the locking plate before the screw can compress the plate to bone and/or the bone across the fracture site.

Intramedullary nails in combination with lag screws or other screw assemblies also have been successfully used to treat fractures of the femur, humerus, tibia, and other long bones as well. A significant application of such devices has been the treatment of femoral fractures. A typical prior art intramedullary nail may have one or more transverse apertures through its distal end to allow distal bone screws or pins to be screwed or otherwise inserted through the femur at the distal end of the intramedullary nail. This is called "locking" and secures the distal end of the intramedullary nail to the femur. In addition, a typical intramedullary nail may have one or more apertures through its proximal end to allow a lag screw assembly to be screwed or otherwise inserted through the proximal end of the intramedullary nail and into the femur. The lag screw is positioned across the break in the femur and an end portion of the lag screw engages the femoral head. An intramedullary nail can also be used to treat shaft fractures of the femur or other long bones.

SUMMARY OF THE INVENTION

The various embodiments of the present invention described below and shown in the Figures provide an implant assembly with an orthopaedic implant, such as an extramedullary plate, and one or more active compression screws for use in fracture healing. The active compression screw includes distal threads for engagement with cancellous bone and also may include proximal threads for engagement with cortical bone. The active compression screw may be threaded into a hole of the orthopaedic implant or otherwise affixed to the implant. Also provided is an instrument and method for implanting the orthopaedic implant assembly.

An implant assembly comprising:
an orthopaedic implant comprising:
at least one compression screw hole comprising a step that provides a location for an instrument to press upon; and
at least one active compression member comprising:
a proximal end portion and a distal end portion, the proximal end portion comprising a head and proximal threads, and the distal end portion comprising distal threads;
an outer tube and an inner slide, at least a portion of the inner slide slides within the outer tube;
a spring and a connecting member that connects the inner slide with the spring; and
a locking member.

The implant assembly of claim 1, wherein the proximal threads have a different pitch than those of the distal threads.

The implant assembly of claim 1, wherein the head is threaded.

The implant assembly of claim 1, wherein the spring is a tension spring and is affixed to both the outer tube and the connecting member.

The implant assembly of claim 1, wherein the at least one active compression member is a non-locking screw.

The implant assembly of claim 1, wherein the at least one active compression member is a helical blade.

The implant assembly of claim 1, further comprising supplemental fixation members and wherein the orthopaedic implant further comprises supplemental fixation holes.

The implant assembly of claim 1, wherein the orthopaedic implant further comprises at least one of a shaft, an instrument hole, an alignment hole, and at least one supplemental fixation hole.

The implant assembly of claim 1, wherein the at least one compression screw hole has a shape selected from the group consisting of cylindrical, frusto-conical, lozenge, navicular, prolated, and combinations thereof.

The implant assembly of claim 1, wherein the at least one compression screw hole has a thread style selected from the group consisting of threaded, partially-threaded, and non-threaded.

The implant assembly of claim 1, wherein the orthopaedic implant further comprises a bone contacting side.

The implant assembly of claim 11, wherein the bone contacting side is shaped to match a surface of a bone.

The implant assembly of claim 12, wherein the bone contacting side has a shape selected from the group consisting of multiple planar segments, splined, multiple curved segments, and arcuate.

A compression device comprising:
a first handle comprising a first pivot hole and at least one cam portion;
a rod holder comprising a channel, a first receiver, and a shaft portion with a locking portion;
a second handle comprising a body portion with a second pivot hole, a second receiver, a chamber, and a passage, the passage adapted to receive the shaft portion;
a pivot pin for placement through the first pivot hole and the second pivot hole;
a release member comprising an engagement portion and a thumb release, the release member configured to move within the chamber, and the engagement portion adapted to engage the locking portion; and
a plate for engagement by the at least one cam portion, the plate comprising a capture hole adapted to receive the shaft portion, wherein the at least one cam portion causes the plate to rotate such that the shaft portion is captured by the capture hole to move the shaft portion axially to change the distance between the first receiver and the second receiver.

A method of applying fracture reduction and/or compression comprising:
inserting a guide wire angularly with respect to the femoral shaft;
placing a drill over the guide wire and drilling into the femur;
removing the drill;
placing a tap into the drilled hole;
connecting a compression device to a rod;
engaging the rod with a step of an orthopaedic implant;
applying pressure to at least one of a first handle and a second handle of the compression device; and
inserting at least one active compression member.

The method of claim x, wherein after applying pressure to at least one of a first handle and a second handle of the compression device, any remaining holes are drilled, tapped, and receive an active compression member.

The method of claim x, further comprising removing the compression device.

The method of claim x, further comprising placing an active compression member in the tapped hole.

The method of claim x, further comprising inserting a compression screw along the guide wire and threadingly securing in the femoral head.

The method of claim x, further comprising securing the implant to the femoral shaft and placing a compression screw in the fractured bone pieces in compression across the fracture.

The method of claim x, further comprising placing an active compression member into the tapped hole.

The method of claim x, further comprising attaching the rod to a self-tapping section.

The method of claim x, further comprising attaching the rod to the tap before placing a tapping section 180 into the tapped hole.

The method of claim x, further comprising attaching an active compression member to the rod instead of the tap.

The method of claim x, wherein placing a tap into the drilled hole includes placing the tap over the guide wire to tap threads.

The method of claim x, wherein engaging the rod with a step of an orthopaedic implant includes pushing the rod holder against the step as pressure is applied to at least one of the first handle and the second handle.

The method of claim x, further comprising watching reduction on fluoroscopy as pressure is applied to at least one of the first handle and the second handle.

The method of claim x, wherein inserting a guide wire angularly with respect to the femoral shaft includes inserting the guide wire through a locking plate hole.

The method of claim x, further comprising driving the guide wire across the bone fracture to reach the cancellous bone of the femoral head.

The method of claim x, further comprising reaming a void in the cortex for receipt of the compression screw to extend through the cortex.

The method of claim x, further comprising selecting an appropriately sized reamer to ream the femoral head.

The method of claim x, further comprising inserting supplemental fixators into supplemental fixation holes.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings which is this case is a group of sketches prepared by the inventor and, which are incorporated in and form a part of the specification, illustrate the embodiments of the invention and together with the written description serve to explain the principles, characteristics, and features of the invention. In the drawings.

DETAILED DESCRIPTION OF THE EMBODIMENTS

The following description of the depicted embodiment(s) is merely exemplary in nature and is in no way intended to limit the invention, its application, or uses.

Figure 2:
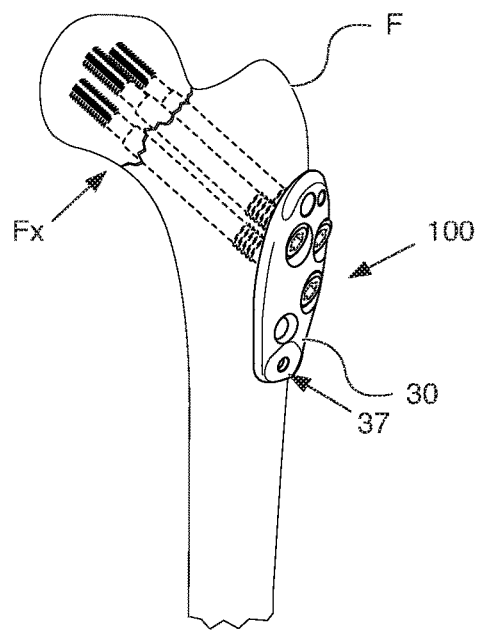
Figure 3:
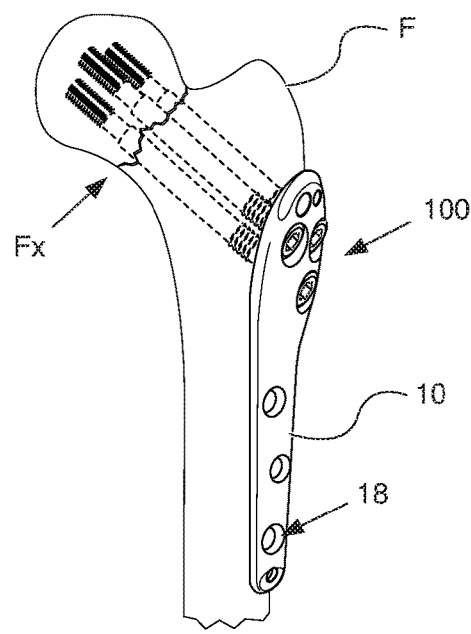

Embodiments of the present invention provide active compression implants that are designed for fracture repair of long bones. FIGS. 2 and 3 show how an implant assembly 100 is typically secured to a portion of a bone for fracture repair.

Figure 1:
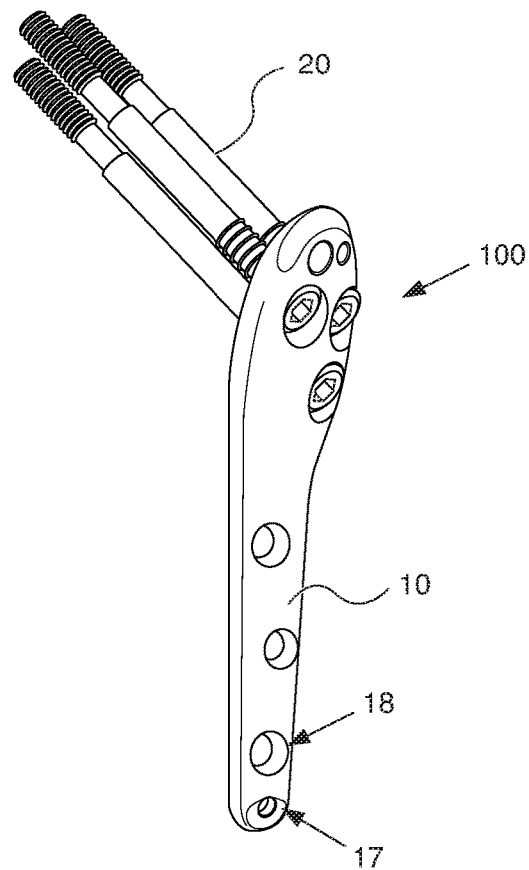
FIGS. 1-3 illustrate an implant assembly.

In a first embodiment, shown in FIGS. 1-12, an implant assembly 100 is disclosed. As best seen in FIG. 1, the implant assembly 100 includes an orthopaedic implant 10 and at least one active compression member 20. Further, while the active compression member 20 is illustrated as a cannulated screw, any surgical screw with appropriate shape, size and properties can be used. In the embodiment illustrated in FIG. 1, the orthopaedic implant 10 is a plate but could equally be another device, such as an intramedullary nail (best seen in FIGS. 19 and 20). Further, there are three active compression members 20 illustrated in the figures but any number of active compression members may be used. Additionally, while the active compression member 20 is illustrated as a screw, those of ordinary skill in the art would understand that the active compression member 20 could equally be a peg or a helical blade (best seen in FIG. 20).

Referring now to FIGS. 2 and 3, the orthopaedic implant assembly 100 is applied to a bone, either internally in the intramedullary canal or externally against cortical bone. In the depicted embodiment, the orthopaedic implant assembly 100 is applied externally against a femur F to repair a fracture Fx. The orthopaedic implant 10, 30 may include a shaft 11 with supplemental fixation holes 18 as shown in FIG. 3 or no shaft as shown in FIG. 2. The active compression member(s) 20 span across the fracture Fx. Fixation holes 18 may be cylindrical, frusto-conical, lozenged, navicular, prolated, or combinations thereof. Fixation holes 18 may be fully-threaded, partially-threaded, or non-threaded.

Figure 4:
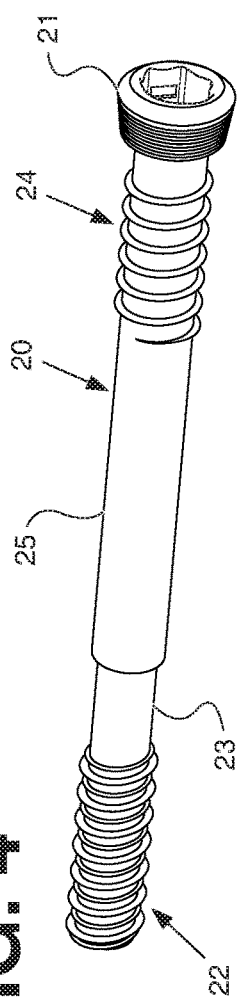
FIGS. 4-6 illustrate an active compression member.
Figure 5:
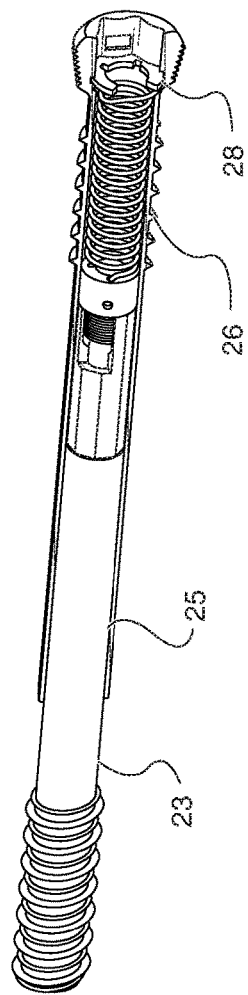
Figure 6:
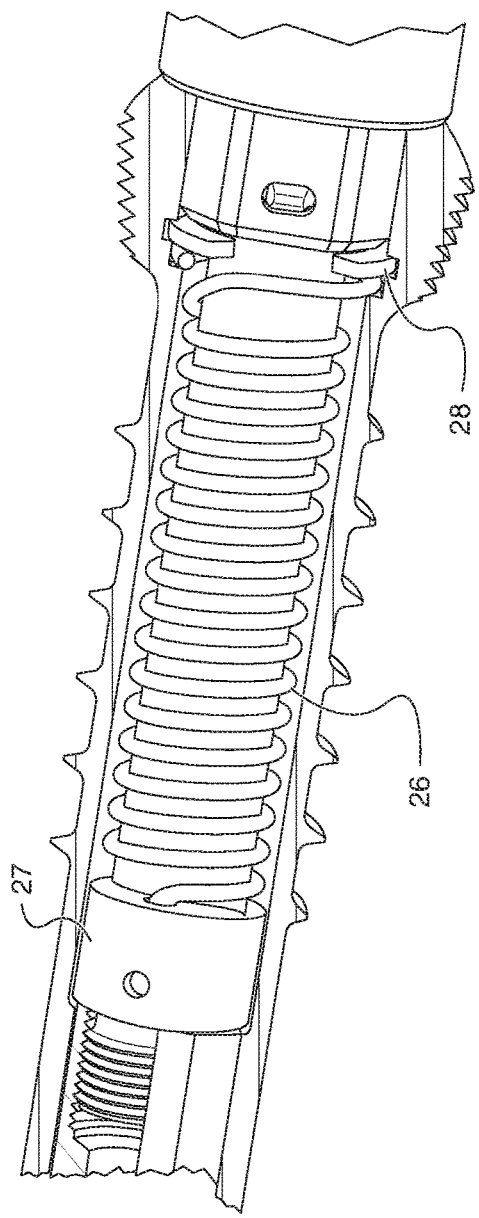

Referring now to FIGS. 4-6, the active compression member 20 may include a head 21, distal threads 22, an inner slide 23, proximal threads 24, an outer tube 25, a spring 26, a connecting member 27, and a locking member 28. The distal threads 22 may engage cancellous bone. The proximal threads 24 may engage cortical bone and/or cancellous bone. The proximal threads 24 may have the same pitch as the distal threads 22. Further, the proximal threads 24 may have the same size threads as the distal threads 22. Those having ordinary skill in the art, however, would understand the pitch may be coarser or finer and that the thread size may be smaller or larger. In the depicted embodiments, the proximal threads 24 are larger and have a different pitch then that of the distal threads 22. The head 21 may be threaded. A portion of the inner slide 23 slides within the outer tube 25. The connecting member 27 connects the inner slide 23 with the spring 26. In the illustrated embodiment, the spring 26 is a tension spring and is affixed to both the outer tube 25 and the connecting member 27, but those of ordinary skill in the art would understand spring 26 could equally be a compression spring adapted to push upon the inner slide 23 toward the head 21.

As mentioned above, in one embodiment the active compression member may be a non-locking screw. It differs from the active compression member 20 described above in that instead of the thread on head 21, the thread is omitted. All other characteristics of this embodiment may be the same as described above.

Figure 20:
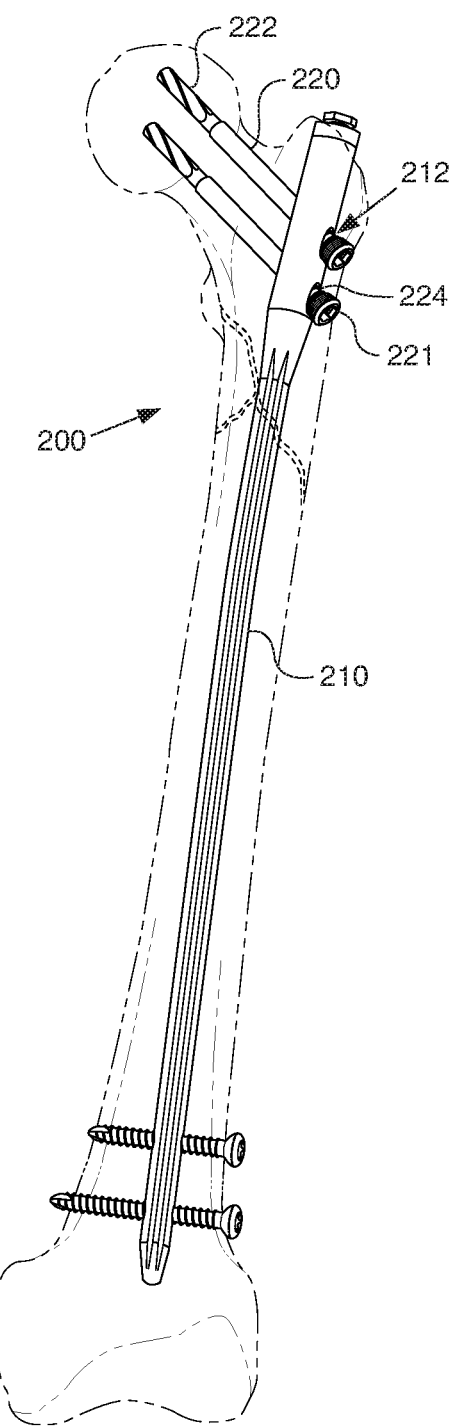

Yet another embodiment of the active compression member is a helical blade. This embodiment differs from the embodiments mentioned above in that, instead of the distal threads 22, the distal section of the screw is a helical blade. FIG. 20 illustrates an example of a active compression member having a helical blade. All other characteristics of this embodiment match the active compression member 20 described above.

Figure 7A:
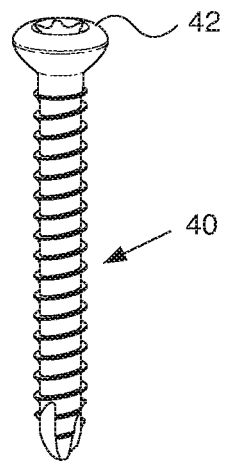
FIGS. 7-8 illustrate supplemental fixation members.
Figure 7B:
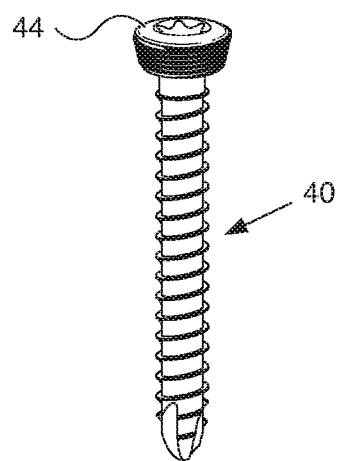
Figure 8:
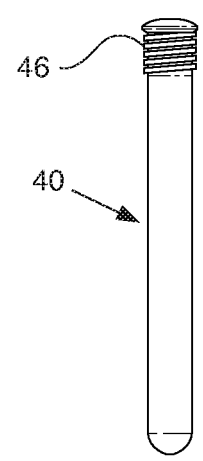

FIGS. 7 and 8 illustrate supplemental fixation members 40 that may be used with supplemental fixation holes 18. The supplemental fixation members may be a non-locking screw 42, a locking screw 44, or a peg 46. In addition, any surgical fastener compatible with an orthopaedic fracture fixation device with appropriate shapes and sizes can be used.

In one embodiment, the orthopaedic implant 10 can be a bone plate. The bone plate can have different shapes and sizes according to the clinical applications.

In one embodiment, the bone plate is a conventional bone plate. In another embodiment, the bone plate is a locking plate. Yet in another embodiment, the bone plate has at least one threaded screw hole to receive a locking screw and at least one non-threaded screw hole to receive a non-locking screw. Characteristics of the locking plate/screws and the non-locking plate/screws may be the same as mentioned above.

Figure 9:
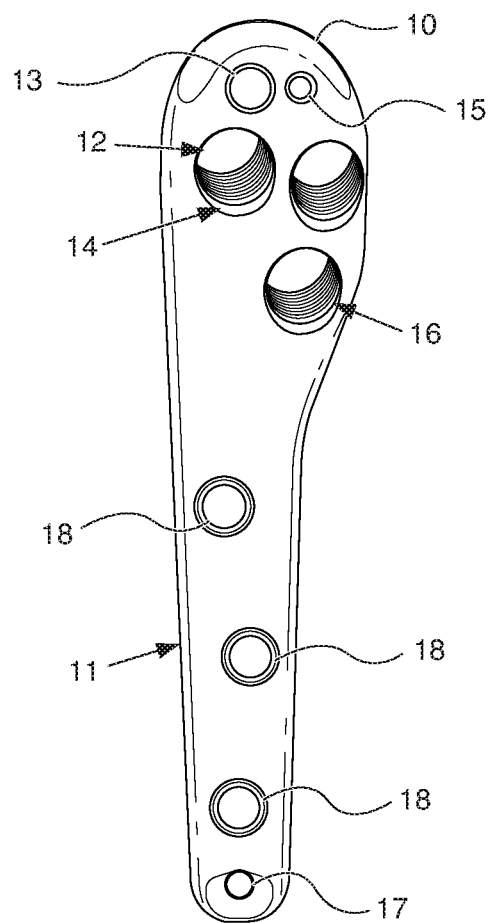
FIGS. 9 and 11 illustrate a first orthopaedic implant.
Figure 11:
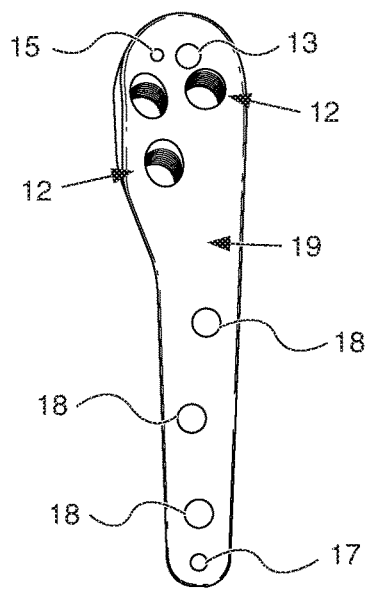

FIGS. 9 and 11 illustrate an embodiment of the orthopaedic implant 10. The implant 10 may have a shaft 11, at least one compression screw hole 12, an instrument hole 13, a step 14, an alignment hole 15, threads 16, one or more supplemental fixation holes 18, and a bone contacting side 19. The compression screw hole 12 may be cylindrical, frusto-conical, lozenged, navicular, prolated, or combinations thereof. The compression screw hole 12 can be threaded, partially-threaded, or non-threaded. Further, if there is more than one compression screw hole, one may be threaded or partially threaded and the other one may be non-threaded. In the depicted embodiment, there are three compression screw holes 12 arranged in a reverse triangle but other hole layouts may equally be used. In some embodiments, the implant 10 may include one or more provisional fixation holes 17. As best seen in FIG. 11, the bone contacting side 19 may be shaped to match the bone. As examples, the bone contacting side 19 may be multiple planar segments, splined, multiple curved segments, or arcuate. The step 14 provides a location for an instrument to press upon as explained in greater detail below.

Figure 10:
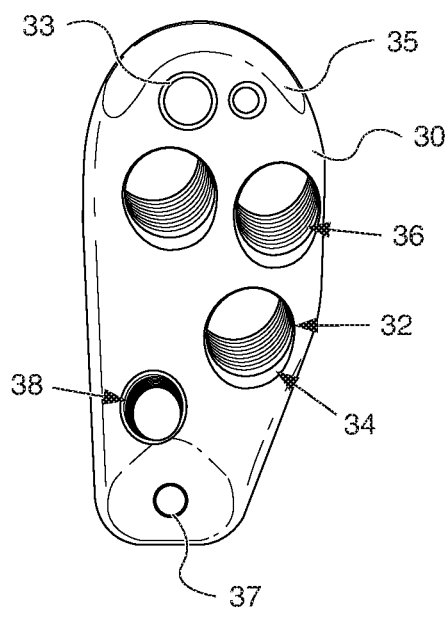
FIGS. 10 and 12 illustrate a second orthopaedic implant.
Figure 12:
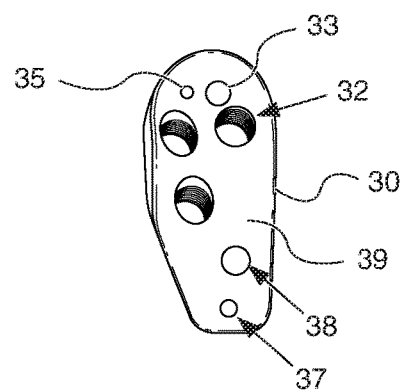

FIGS. 10 and 12 illustrate another embodiment of the orthopaedic implant 30. The implant 30 may have at least one compression screw hole 32, an instrument hole 33, a step 34, an alignment hole 35, threads 36, and a bone contacting side 39. In some embodiments, the implant 30 may include one or more provisional fixation holes 37. The fixation holes 37 can be either threaded or non-threaded. As best seen in FIG. 12, the bone contacting side 39 may be shaped to match the bone. As examples, the bone contacting side 39 may be multiple planar segments, splined, multiple curved segments, or arcuate. The step 34 provides a location for an instrument to press upon as explained in greater detail below.

The instrument hole 13, 33 allows the orthopaedic implant to connect to an instrument. For example, the connection may be through a pin, peg, or screw. Further, the alignment hole 15, 35 may be used to orient the orthopaedic implant relative to an instrument. The alignment hole 15, 35 may be sized and shaped to receive a pin, peg, or screw. In some embodiments, instrument hole 13, 33 and/or alignment hole 15, 35 may be omitted.

In some embodiments, a compression device is provided. In general, any compression device with appropriate sizes and shapes that buttresses against the bone plate and pulls a tapping section of the device axially back out of the compression screw hole 12, 32 can be used.

Some embodiments include an instrument for a bone plate that has a self-tapping thread section, an integral rod section, and a compression device. In general, any compression device with appropriate size, shape and properties can be used. The instrument for a bone plate can be inserted through one of the plurality of threaded or unthreaded plate holes of the plate. Non-limiting examples of compression device are illustrated in U.S. Pat. Nos. 4,456,005, 7,135,023, 7,503, 919, which describe compression members of a compression bone fixation device that draws a threaded screw axially, which compresses the fracture site for use in the treatment of fractures.

Figure 13:
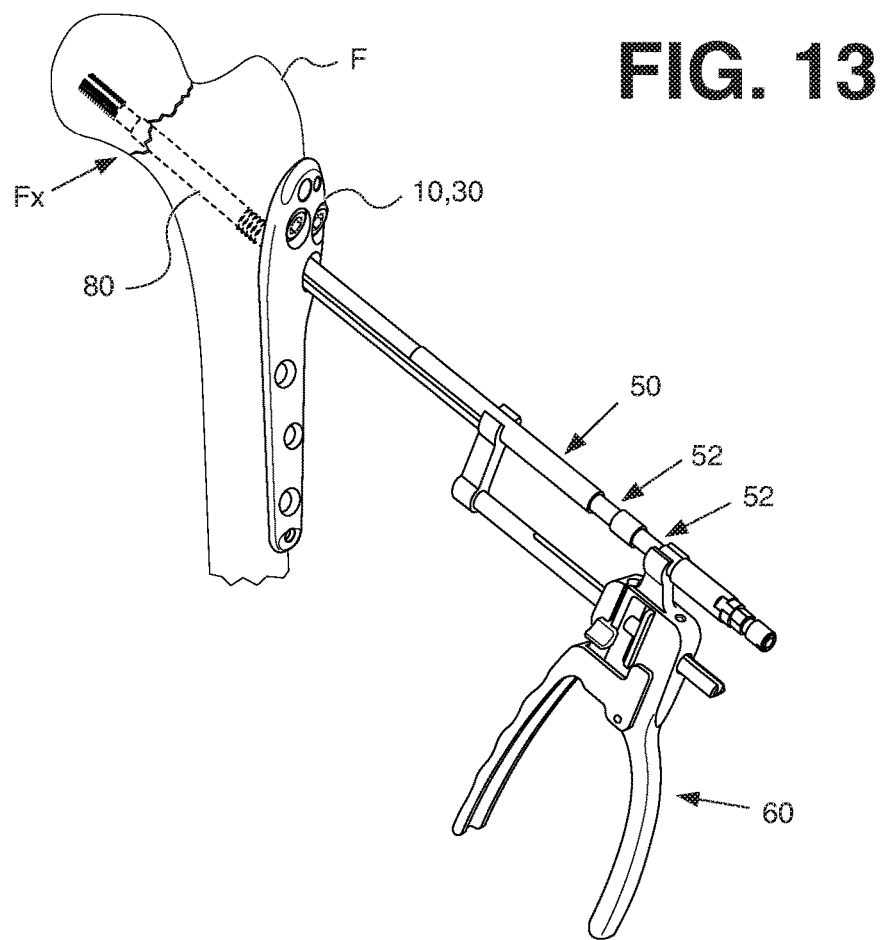
FIGS. 13-18 illustrate instruments and a method for implanting the implant assembly.

In some embodiments, FIGS. 13-16 illustrate instruments for the implant 10, 30. FIG. 13 illustrates a rod 50 and a compression device 60. In some embodiments, the rod 50 has at least one recess 52 such that the rod is assembled to the compression device 60 through the use of the at least one recess 52.

Figure 14:
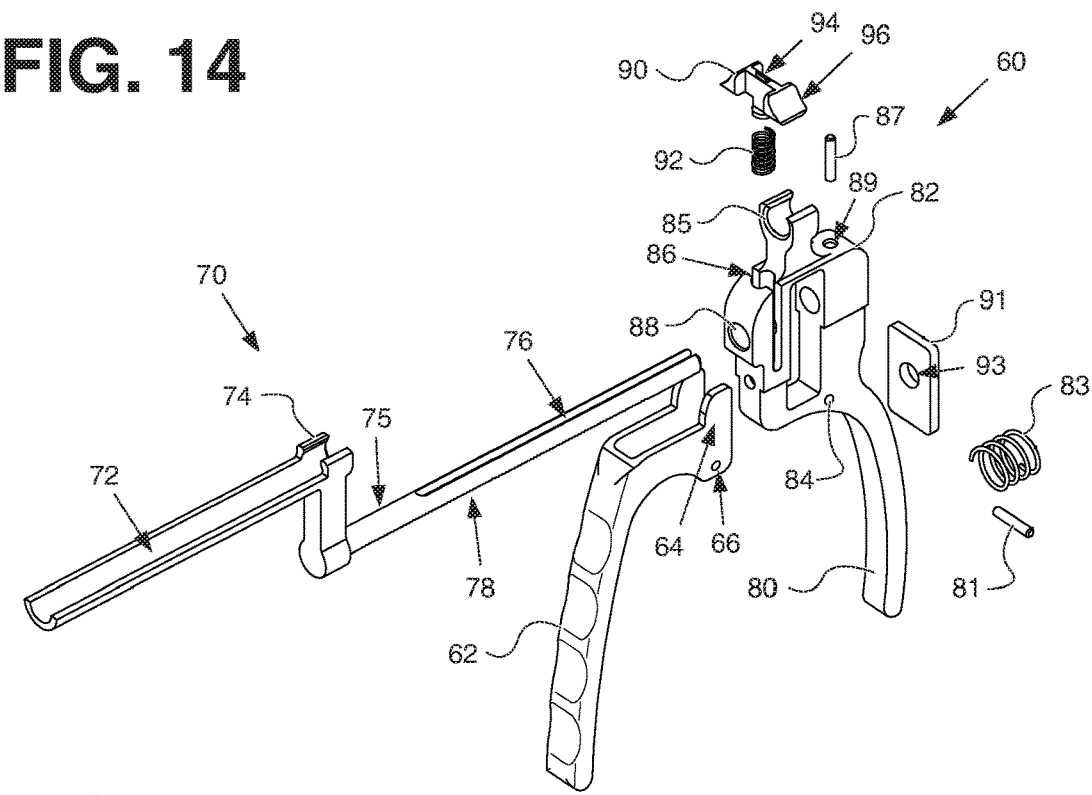

As best seen in FIG. 14, the compression device 60 may have a first handle 62, a rod holder 70, a second handle 80, a pivot pin 81, a first spring 83, a clocking pin 87, a release member 90, a plate 91, and a second spring 92. The first handle 62 has a first pivot hole 66 and one or more cam portions 64. The rod holder 70 has a channel 72, a first receiver 74, and a shaft portion 75. The shaft portion 75 has a groove 76 and a locking portion 78. The shaft portion 75 may be square, round, or D-shaped. The locking portion 78 may comprise teeth, such as ratchet teeth. The second handle 80 includes a body portion 82. The body portion 82 has a second pivot hole 84, a second receiver 85, a chamber 86, a passage 88, and a clocking hole 89. The passage 88 may be square, round, or D-shaped and may or may not match the shape of the shaft portion 75. In some embodiments, the slot 76, the clocking pin 87, and the clocking hole 89 may be eliminated. The plate 91 includes a capture hole 93. The release member 90 has an engagement portion 94 and a thumb release 96. In the depicted embodiment, there is a thumb release 96 on each side of the release member 90 but in other embodiments the thumb release 96 may be provided only on one side.

For assembly of the compression device 60, the clocking pin 87 is inserted into the clocking hole 89, the second spring 92 is placed in the chamber 86, and the release member 90 is placed in the chamber 86 over the second spring 92. The shaft portion 75 is inserted into the passage 88, over the release member 90, into the first spring 83, through the capture hole 93 of the plate 91, and through the remainder of the passage 88 such that the groove 76 engages the clocking pin 87. The first spring 83 presses against the plate 91, and the second spring 92 presses against the release member 90 such that the engagement portion 94 contacts or engages the locking portion 78. The first handle 62 is placed such that the first pivot hole 66 is aligned with the second pivot hole 84 and the cam 64 engages the plate 91. Once aligned, the pivot pin 81 is inserted into the pivot holes 66, 84.

In use, a user applies pressure to the first handle 62 and/or the second handle 80. The first handle 62 rotates about the pivot pin 81, which causes the cam 64 to engage the plate 91. The cam 64 causes the plate 91 to rotate such that the shaft portion 75 is captured or pinched by an upper and lower portion of the capture hole 93. As the first handle 62 continues to rotate, the captured shaft portion 75 is moved axially while the locking portion 78 slides over the release member 90 to change the distance between the first receiver 74 and the second receiver 85. When rotation stops, either by the user or mechanical limits, the cam 64 disengages from the plate, the plate 91 releases the shaft portion 75, and the engagement portion 94 engages the locking portion 78 to maintain the relative positions of the first and second receivers 74, 85. When desired, a user may press upon the thumb release 96 to allow the release member 90 to disengage from the locking portion 78 such that the rod holder 70 may slide relative to the handles 62, 80.

Figure 15:
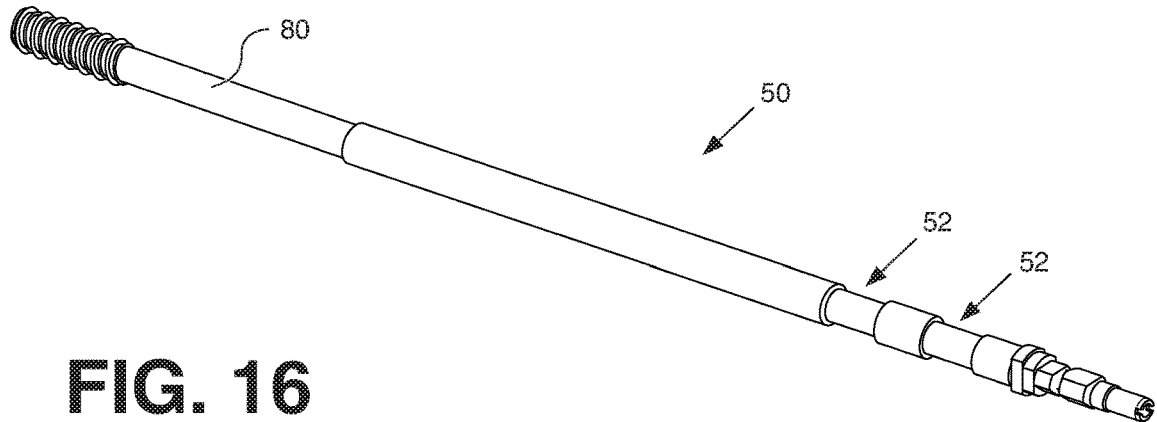
Figure 16:
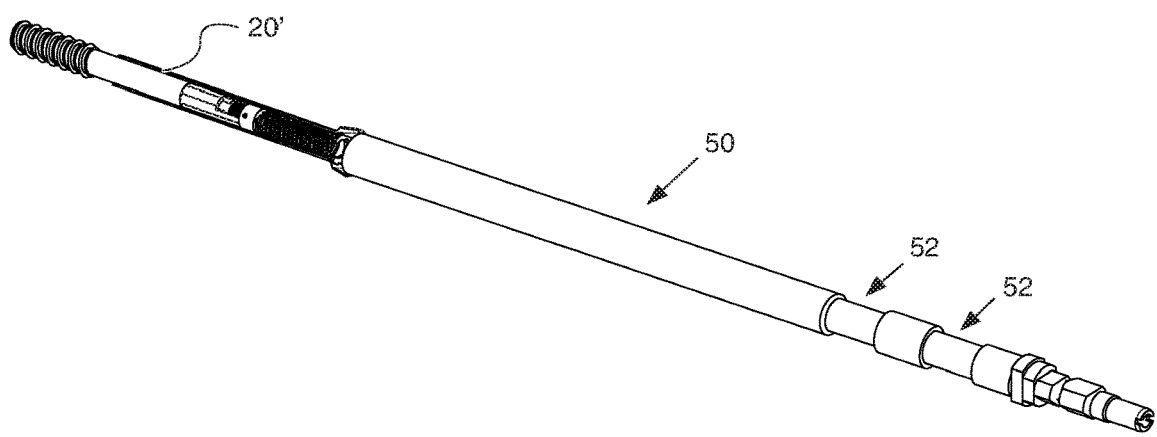

FIGS. 15-16 illustrate the embodiments of the rod 50. In FIG. 15, the rod has a tapping section 80. The tapping section 80 may be monolithic, composite, or modular. In FIG. 16 the rod 50 is connected to a compression member 20'. The compression member 20' is the same as those depicted above except the proximal threads for engaging cortical bone are omitted.

Figure 17:
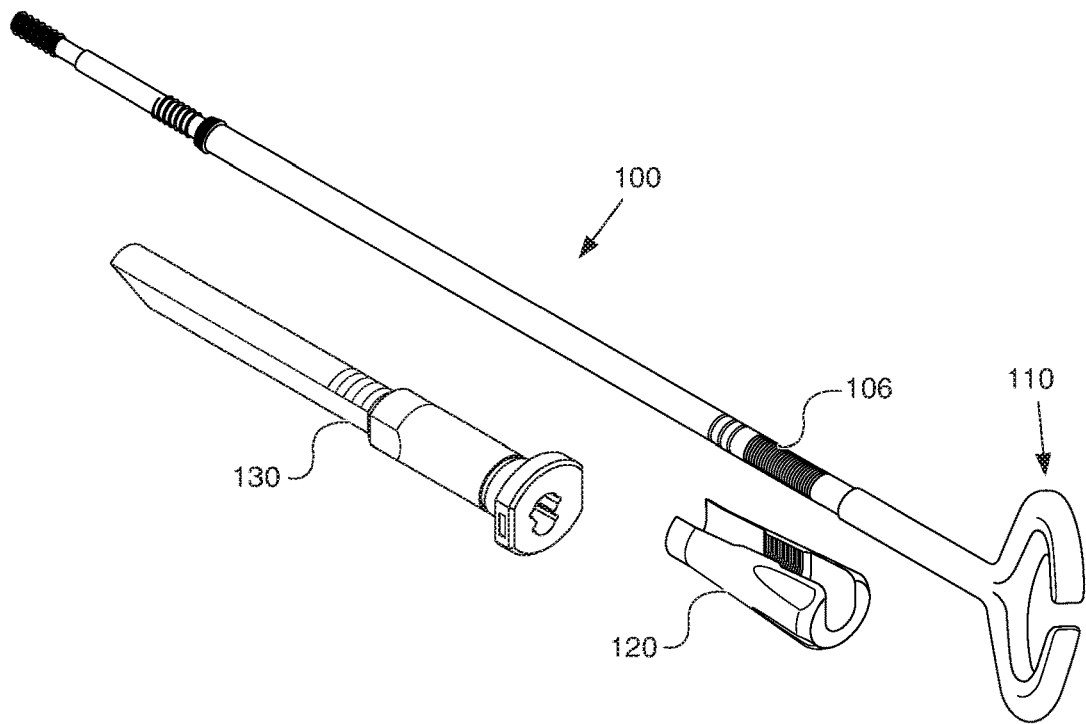
Figure 18:
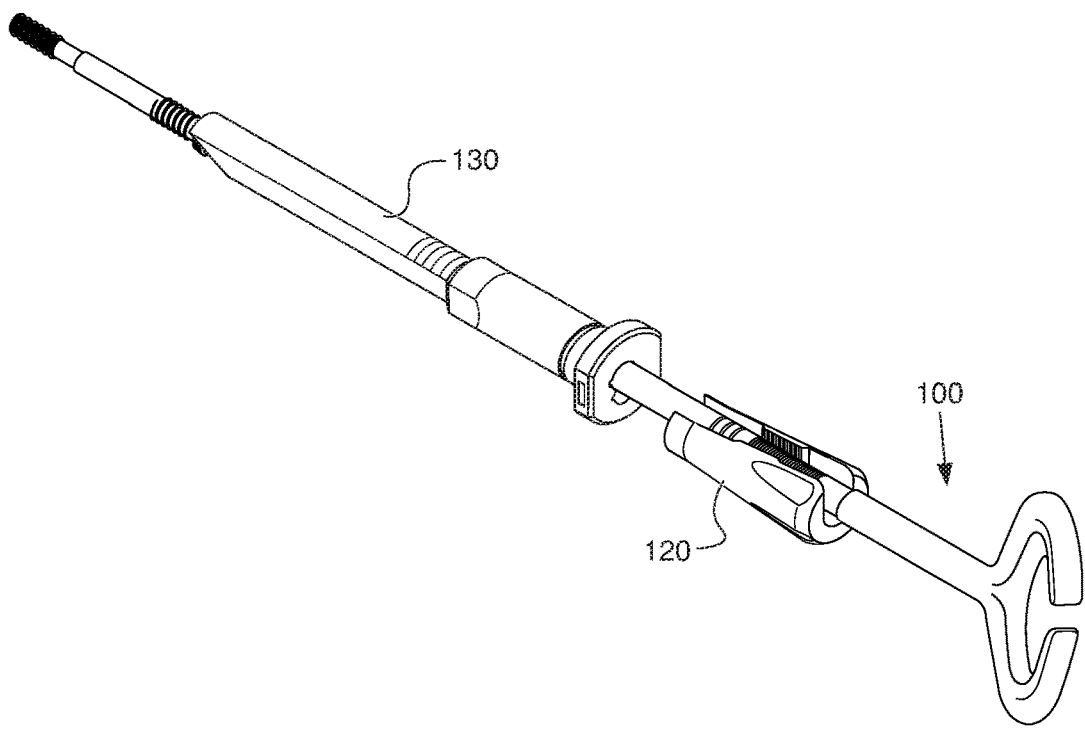

While the FIGS. 13-14 illustrate the compression device 60, those of ordinary skill in the art would understand that other mechanisms may be used to reduce the fracture and apply compression. As best seen in FIGS. 17-18, a rod 100 is used to reduce the fracture and apply compression. The rod 100 is the same as rod 50 except it has a threaded section 106 and a handle 110. The rod 100 may have a tap section or compression member as described above. FIGS. 17-18 also illustrate a drill guide tube 120 and a nut 130. The rod 100 engages the bone fragment, through the tap section or the compression member, and the drill guide tube 120 is placed over the rod 100. The drill guide tube 120 pushes against the implant. The nut 130 is placed over the rod 100 and is rotated to engage the threaded section 106. The nut 130 uses the thread section 106 to push on the drill guide tube 120 and pull on the rod 100 to reduce and/or compress the fracture.

As another example, a user could pull on the rod 100 using the handle 110 to manually reduce the fracture. Further, the user could apply a clamp (not shown) to the rod 100 to hold compression while implanting one or more active compression members 20 after manually reducing the fracture.

In some embodiments, the compression device may be inserted into a patient by any suitable known technique. Generally, correct positioning of the nail or plate is critical to ensure that the screws are placed in the center of the femoral head. A guide wire is inserted angularly with respect to the femoral shaft. The guide wire is driven across the bone fracture to reach the cancellous bone of the femoral head. Optionally, according to the position of the guide wire, an appropriate reamer is used to ream a void in the cortex for receipt of the compression screw to extend through the cortex. An appropriate sized reamer can be selected to ream the femoral head. For example, the reamer can be 5 mm, 7 mm, or 9 mm in diameter. The correct depth for reaming is less than the length of the guide wire to reduce the likelihood of the guide wire being removed with the reamer. The compression screw is inserted along the guide wire and threadingly secured in the femoral head. The implant is secured to the femoral shaft and a compression screw can place the fractured bone pieces in compression across the fracture.

In some embodiments, a guide wire is placed through one of the locking plate holes 12. In the depicted embodiment, the guide wire is placed through the bottom hole. A drill is placed over the guide wire and drills through the compression hole, into the femur F, and across the fracture site, using the guide wire for guidance. The drill is removed. A tap is placed over the guide wire to tap threads into the drilled hole. In some methods, the guide wire may be removed before tapping. An active compression member 20 is placed into the tapped hole. The rod 50 is attached to a self-tapping section 180. In some methods, the rod 50 may be attached before the tapping section 180 is placed into the tapped hole. In some methods, an active compression member may be connected to the rod instead of the tap. The compression device 60 is connected to the rod 50. A user squeezes the first and second handles 62, 80 to apply force to the active compression member 20. As the user squeezes the handles 62, 80, the rod holder 70 pushes against the step 14, 34. The user watches on fluoroscopy while squeezing the handles 62, 80 to see the bone fragments being reduced. In some methods, as noted above, the active compression member 20 may be used to reduce the fracture instead of the tap. After reduction, the remaining holes 12 are drilled, tapped, and receive an active compression member 20. In some methods, the remaining holes 12 can receive any bone screws that have appropriate sizes and shapes. The compression device 60 is removed. If necessary, an active compression member 20 is placed in the compression screw hole 12 that is used for reduction. Thereafter, supplemental fixators 40 may be inserted in the supplemental fixation holes 18.

In another method, at least one active compression member is inserted into bone such that threads 24 are engaged as described above but the active compression member is not locked to the bone plate. The user applies the compression device 60 to reduce the fracture, and the user then inserts the active compression member to lock the compression member to the plate, all while maintaining reduction.

Those of ordinary skill in the art would understand that the threads 16, 21, 36 are a convenient way to lock the active compression member 20 to the plate 10, 30, but there are other ways to achieve the same function. For example, a cover plate attached to the bone plate could be used to lock the active compression member in place. As another example, a "manhole cover" could thread into the bone plate over the active compression member to lock it in place.

Figure 19:
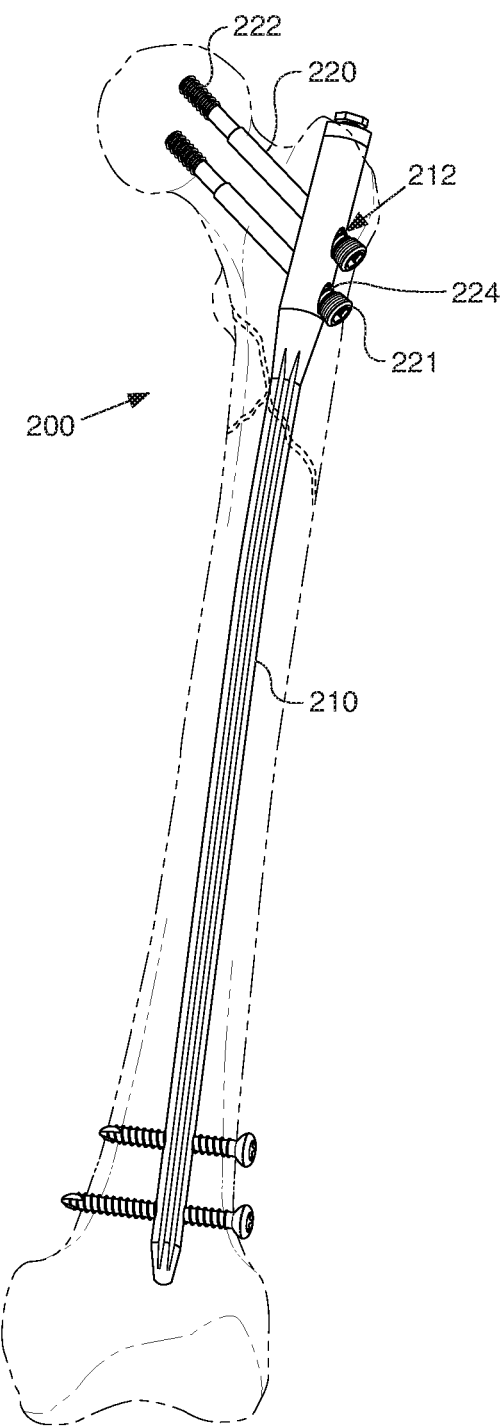
FIGS. 19-20 illustrate an alternative embodiment of the orthopaedic implant.

FIGS. 19-20 show an implant assembly 200. The implant assembly 200 includes an orthopaedic implant 210 and at least one active compression member 220. The orthopaedic implant 210 has at least one compression hole 212. Further, while the active compression member 220 is illustrated as a cannulated screw, any surgical screw with appropriate shape, size and properties can be used. In the embodiment illustrated in FIGS. 19-20, the orthopaedic implant 210 is an intramedullary nail. Further, there are two active compression members 220 illustrated but any number of active compression members may be used. Additionally, while the active compression member 220 is illustrated as a screw in FIG. 19, the active compression member 220 could equally be a peg or a helical blade, as shown in FIG. 20. In some embodiments, there is provided only a limited amount of clearance between the active compression member 220 and the compression hole 212 so the compression member 220 has a reduced likelihood of toggling.

The active compression member 220 may have a head 221, distal threads or helical blade 222, and proximal threads 224. The distal threads 222 may engage cancellous bone. The proximal threads 224 may engage cortical bone and/or cancellous bone. The proximal threads 224 may have the same pitch as the distal threads 222. Further, the proximal threads 224 may have the same size threads as the distal threads 222. Those having ordinary skill in the art, however, would understand the pitch may be coarser or finer and that the thread size may be smaller or larger. In the depicted embodiments, the proximal threads 224 are larger and have a different pitch then that of the distal threads 222. In some embodiments, the proximal threads 224 may be adjacent to the head 221 to ensure purchase into cancellous bone. In yet other embodiments, the proximal threads 224 may be omitted. The head 221 may or may not be threaded.

The head 221 may be threaded to lock the active compression member to the intramedullary nail. Alternatively, one or more set screws in the intramedullary nail cannulation may be used to lock each active compression member. Additionally, the active compression member may be locked through the use of: an offset or eccentric hole, a sleeve, a sliding insert, a hole that deforms when the active compression member is tightened, or a collet.

Figure 21:
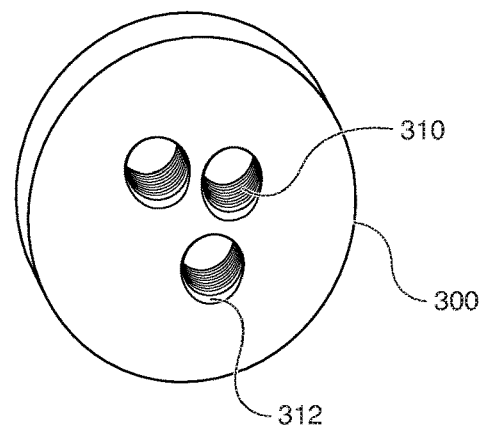
FIGS. 21-22 illustrate a disk instrument and its use.
Figure 22:
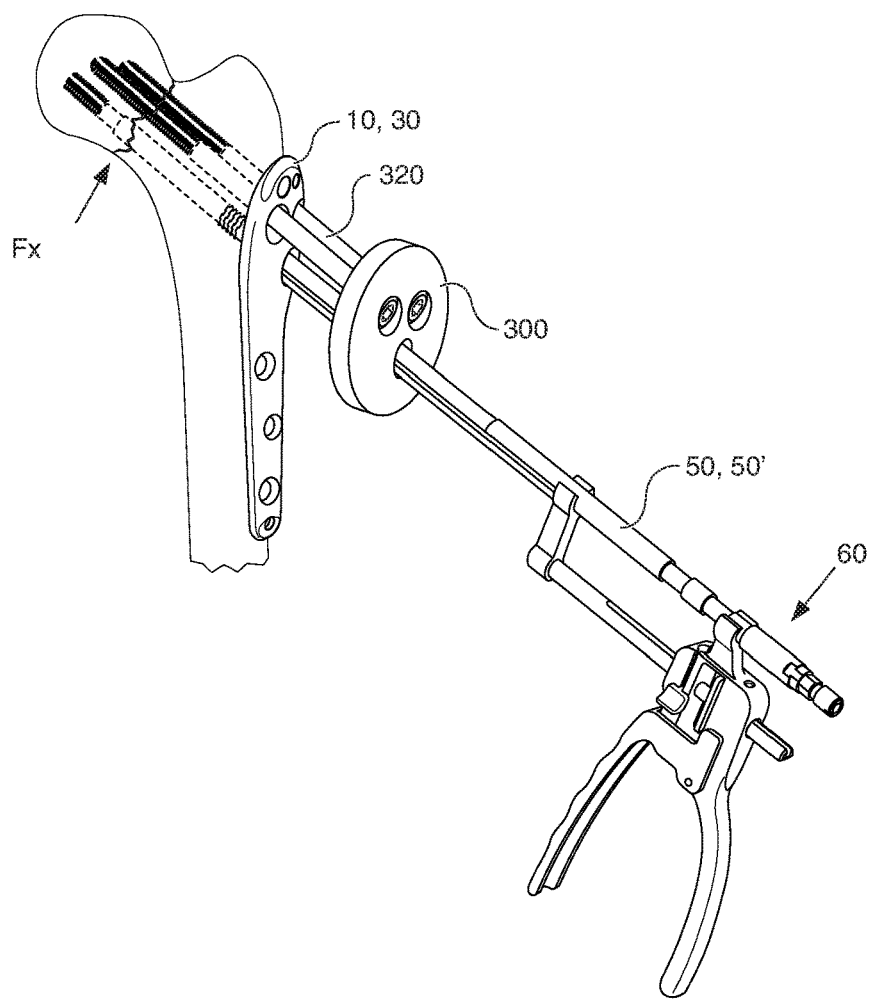

Referring now to FIGS. 21-22, there is provided a disk 300. In some instances, it may be desirable to reduce the fracture Fx with more than one tap or compression member so as not to apply a moment to the fracture fragment. The disk 300 allows a user to reduce the fracture evenly and without applying a moment. The disk 300 has holes 310 and the same hole pattern as the implant 10, 30. The holes 310 may or may not be threaded. Further, holes 310 may or not include a step 312 to receive the rod 50. While FIGS. 21-22 illustrate the disk 300 as being cylindrical, other shapes, such as rectangular or triangular, could equally be used.

FIG. 22 illustrates the fracture Fx, the implant 10, 30, the rod 50', and the compression device 60. As noted above, other compression devices and methods may be used. In a first embodiment, three taps are placed into the fracture fragment, the disk 300 is placed over the taps and against the implant 10, 30, the rod 50 is connected to one of the taps, and the compression device 60 is used to reduce the fracture and apply compression. In a second embodiment, the disk 300 has one non-threaded hole and two threaded holes, the rod and tap are inserted through the non-threaded hole, screws, taps, or alignment pegs 320 are connected to the threaded holes and the fracture fragment, and the compression device 60 is used to apply compression and reduce the fracture. In a third embodiment, the disk 300 is connected to the rod 50', such as by threads or a stop, such that as the compression device 60 pulls back on the rod 50' the disk 300 is also pulled back, screws, taps, or alignment pegs 320 are connected to the threaded holes and the fracture fragment, and the compression device is used to apply compression and reduce the fracture.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the invention should not be limited by any of the above-described exemplary embodiments, but should be defined only in accordance with the claims and their equivalents.

Throughout this document, various references are mentioned. All such references are incorporated herein by reference.

What is claimed is:

1. A compression device comprising:
   a. a first handle comprising a first pivot hole and at least one cam portion;
   b. a rod holder comprising a channel, a first receiver, and a shaft portion with a locking portion;
   c. a second handle comprising a body portion with a second pivot hole, a second receiver, a chamber, and a passage, the passage adapted to receive the shaft portion;
   d. a pivot pin for placement through the first pivot hole and the second pivot hole;
   e. a release member comprising an engagement portion and a thumb release, the release member configured to move within the chamber, and the engagement portion adapted to engage the locking portion; and
   f. a plate for engagement by the at least one cam portion, the plate comprising a capture hole adapted to receive the shaft portion, wherein the at least one cam portion causes the plate to rotate such that the shaft portion is captured by the capture hole to move the shaft portion axially to change the distance between the first receiver and the second receiver.

\* \* \* \* \*